United States Patent [19]

Armstrong et al.

[11] Patent Number: 4,553,934
[45] Date of Patent: Nov. 19, 1985

[54] FORCE-ADJUSTABLE AND DISCONNECTIBLE CONNECTOR FOR ORTHODONTIC HEADGEAR

[75] Inventors: Maclay M. Armstrong, 17001 - 14th Northwest, Seattle, Wash. 98177; Steven A. Houser, Everett, Wash.

[73] Assignee: Maclay M. Armstrong, Seattle, Wash.

[21] Appl. No.: 606,073

[22] Filed: May 1, 1984

Related U.S. Application Data

[63] Continuation-in-part of Ser. No. 573,100, Jan. 23, 1984.

[51] Int. Cl.⁴ .............................................. A61C 7/00
[52] U.S. Cl. ......................................................... 433/5
[58] Field of Search ............................................ 433/5

[56]  References Cited

U.S. PATENT DOCUMENTS

| | | |
|---|---|---|
| 702,805 | 6/1902 | Lindas ........................................ 433/5 |
| 3,526,035 | 9/1970 | Armstrong . |
| 3,772,789 | 11/1973 | DeWoskin .............................. 433/5 |
| 4,115,921 | 9/1978 | Armstrong . |
| 4,155,161 | 5/1979 | Armstrong . |
| 4,226,589 | 10/1980 | Klein . |
| 4,238,188 | 12/1980 | Armstrong .............................. 433/5 |
| 4,368,039 | 1/1983 | Armstrong . |
| 4,416,625 | 11/1983 | Armstrong . |

Primary Examiner—Robert Peshock
Attorney, Agent, or Firm—Robert W. Beach; Ward Brown

[57]  ABSTRACT

A connector for orthodontic headgear includes a casing for a helical compression spring one end of which engages the head of a rod extending through the spring and through a sleeve which engages the other end of the spring. The sleeve is supported in an aperture in the end of the casing and is adjustable axially relative to the casing for adjusting the spring force. The connection is disconnectible by providing a metal clip securable to a headcap having legs engageable in grooves in the casing.

16 Claims, 36 Drawing Figures

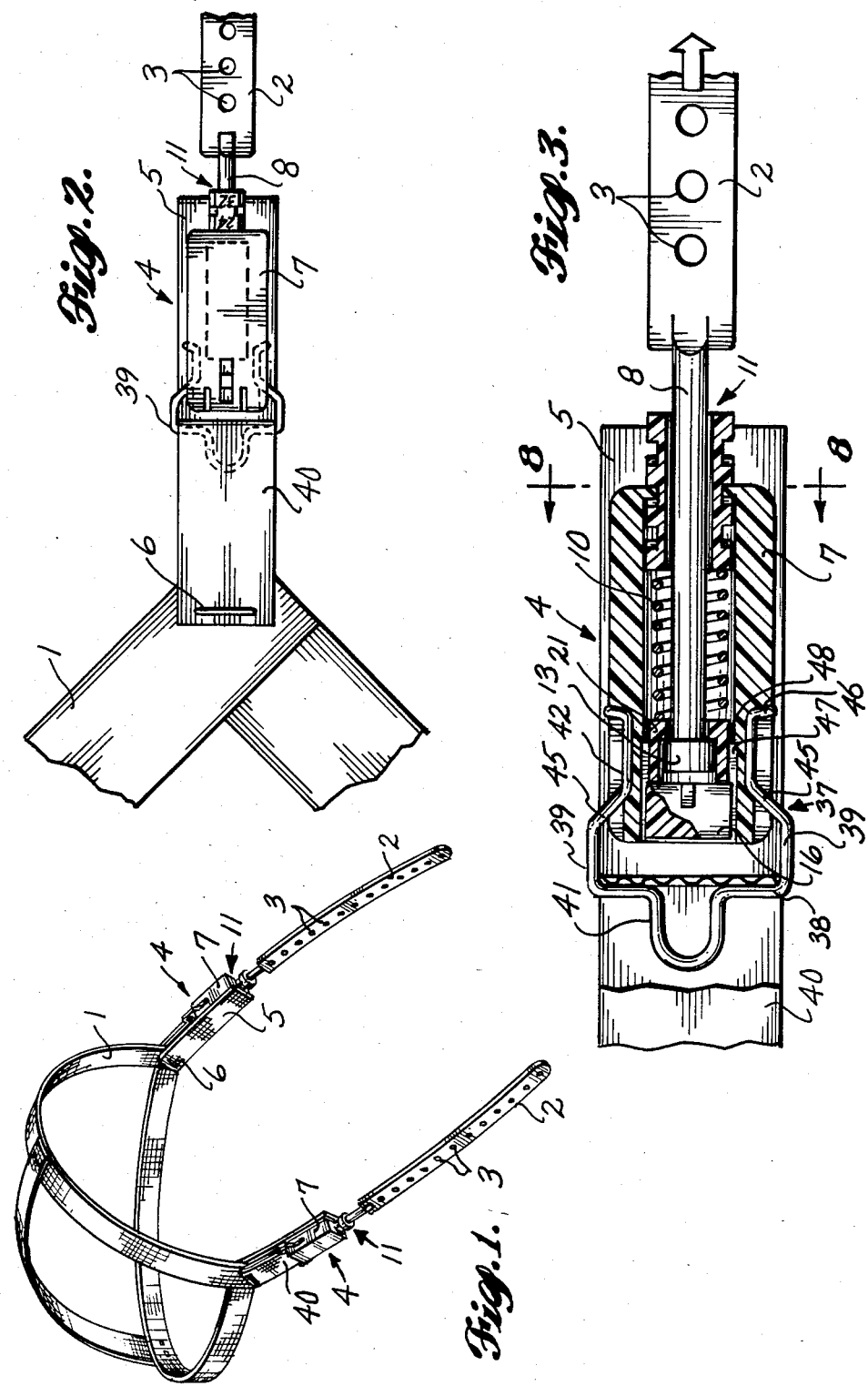

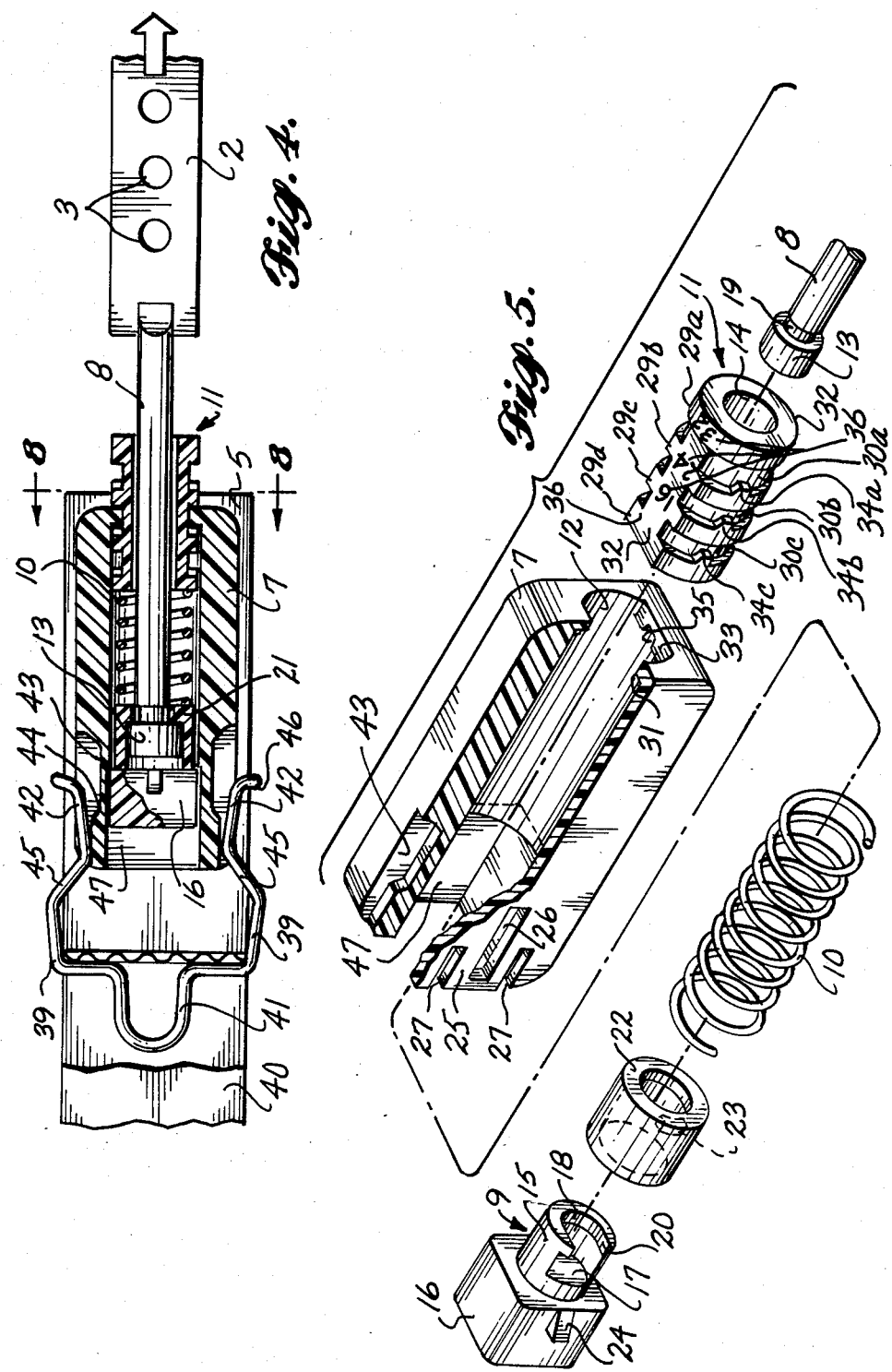

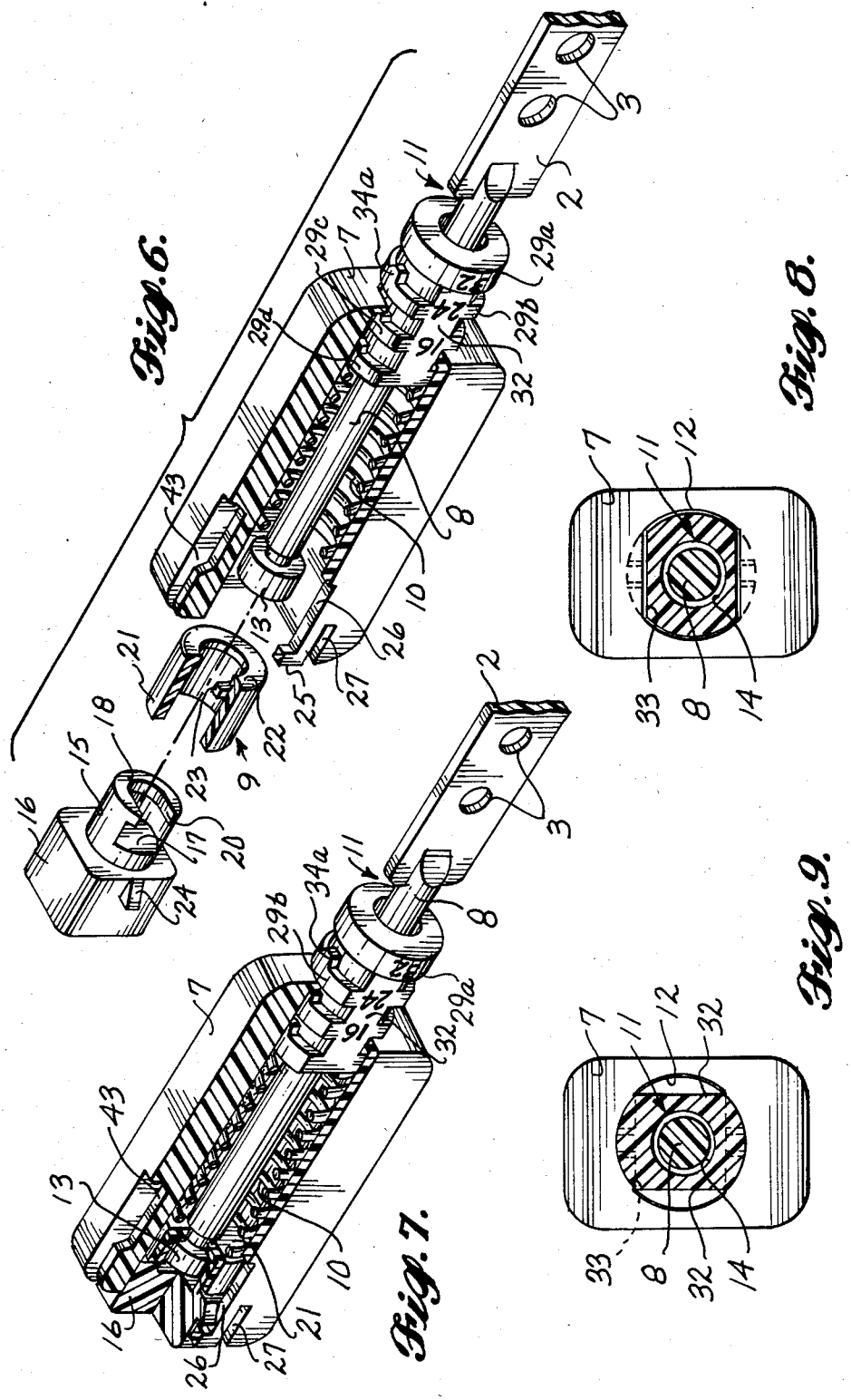

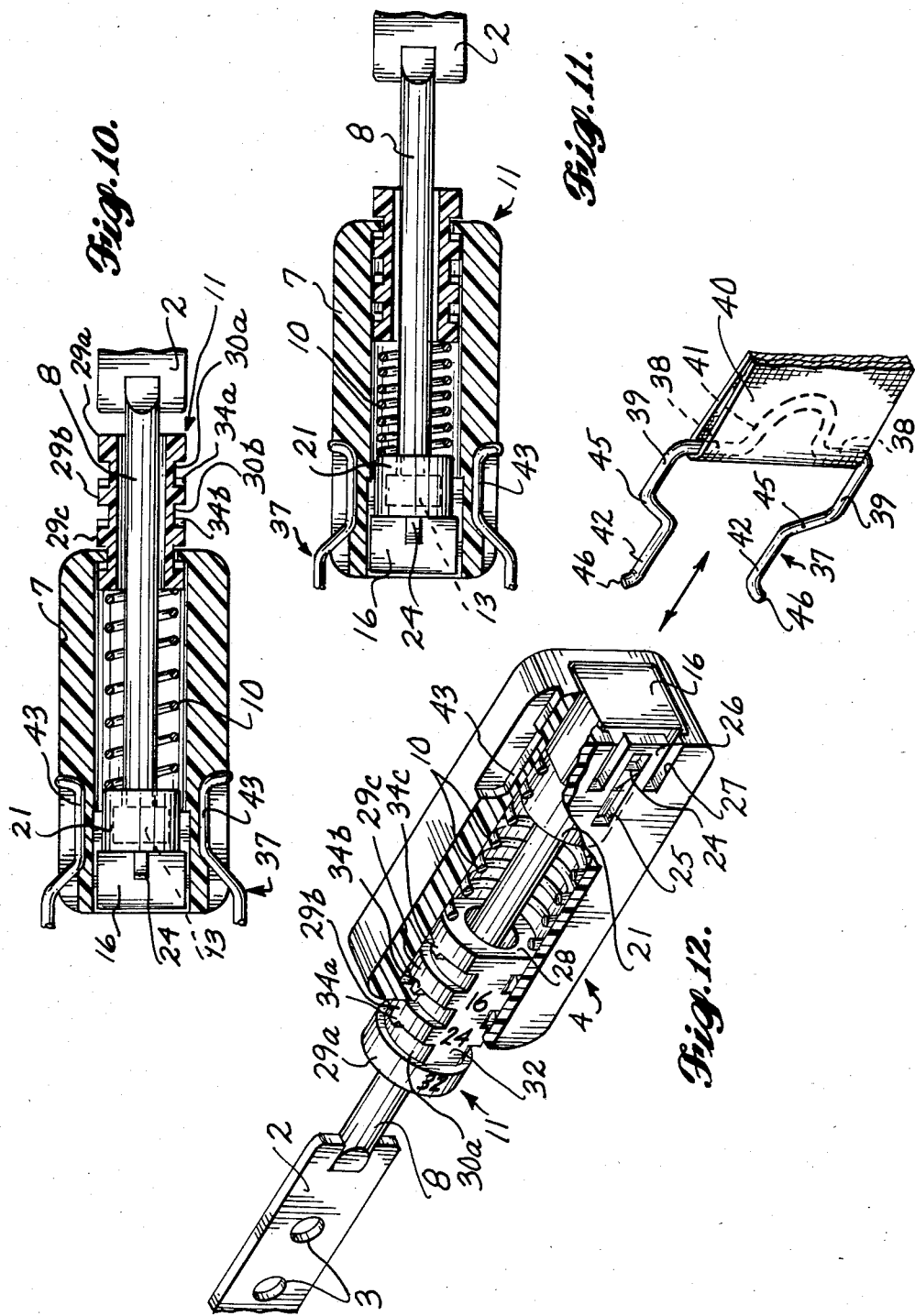

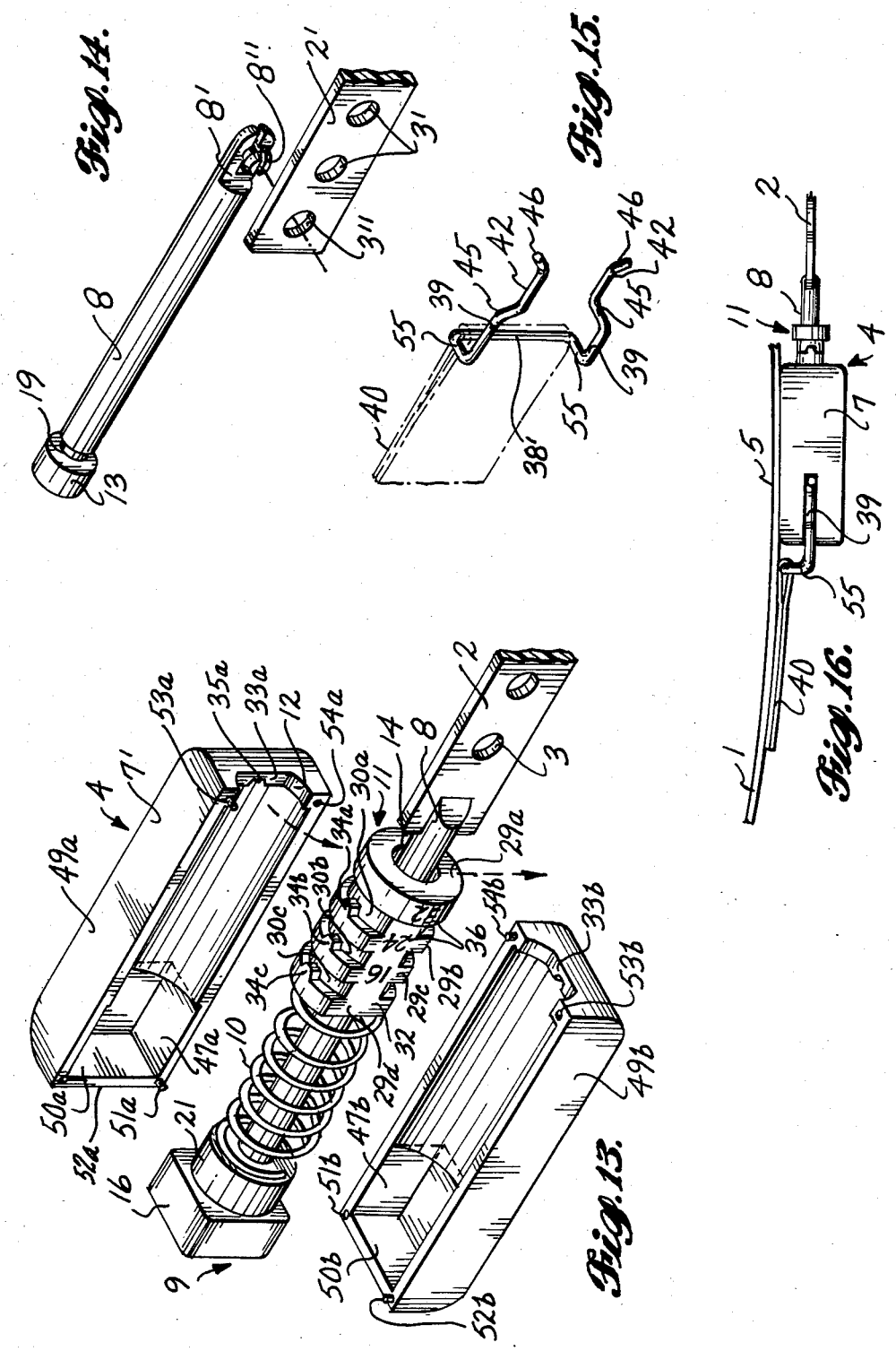

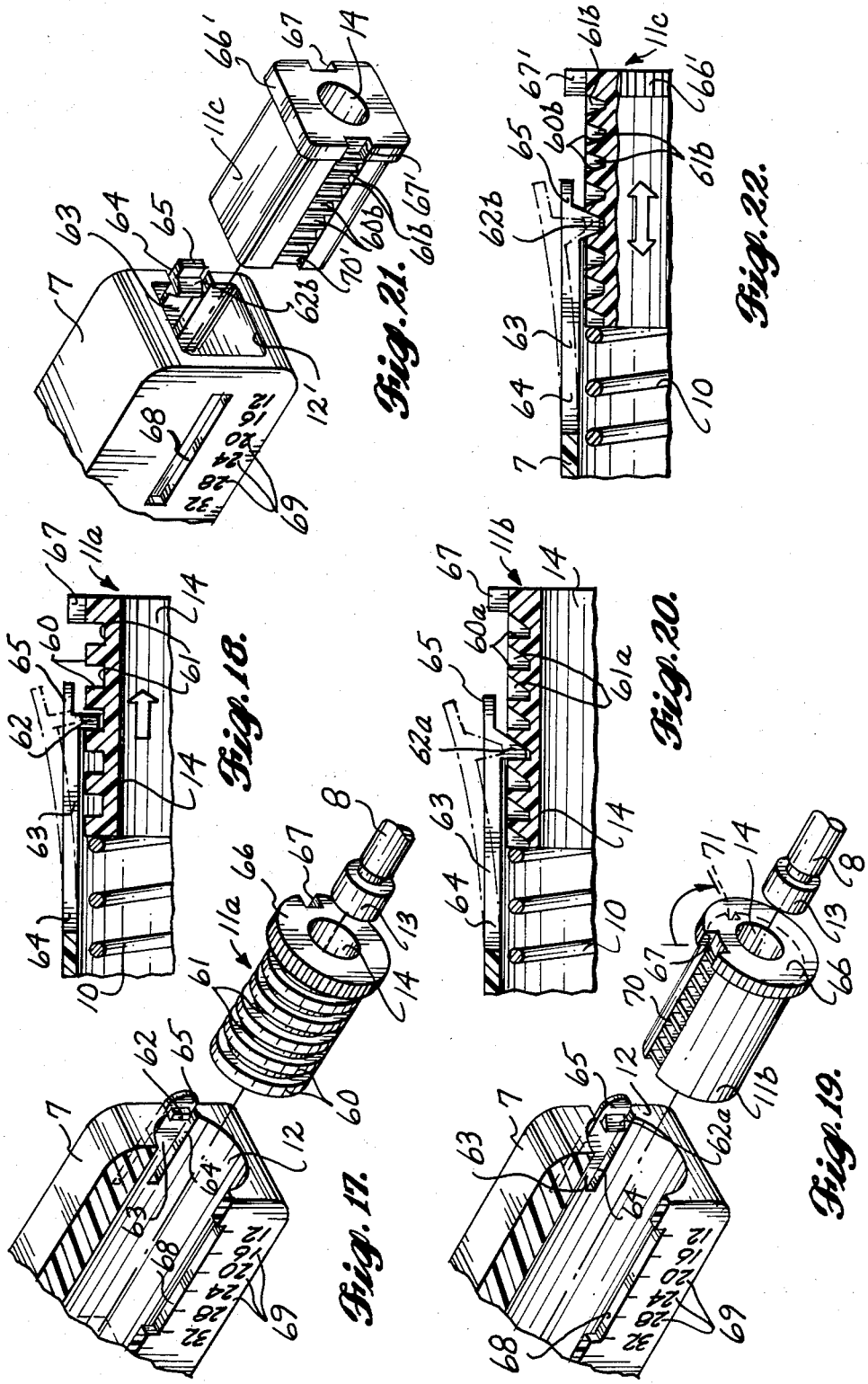

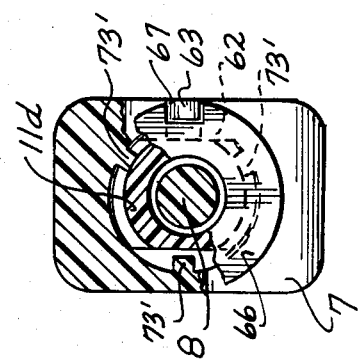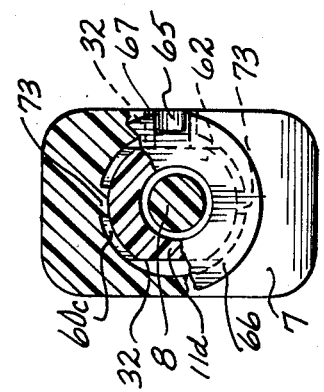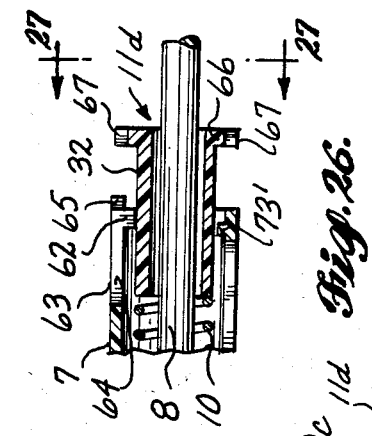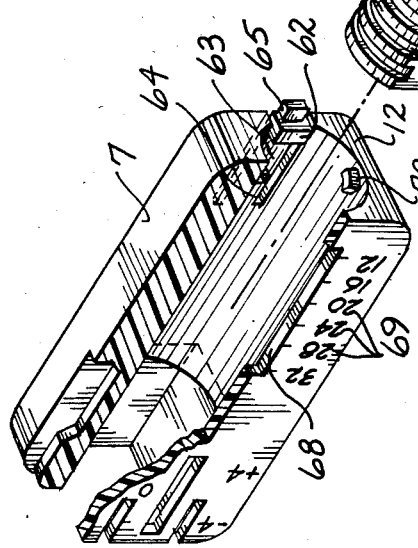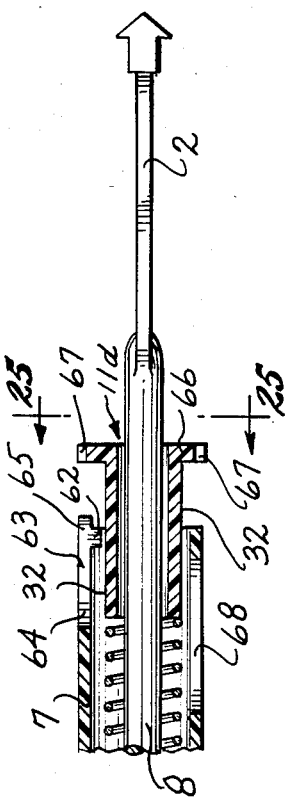

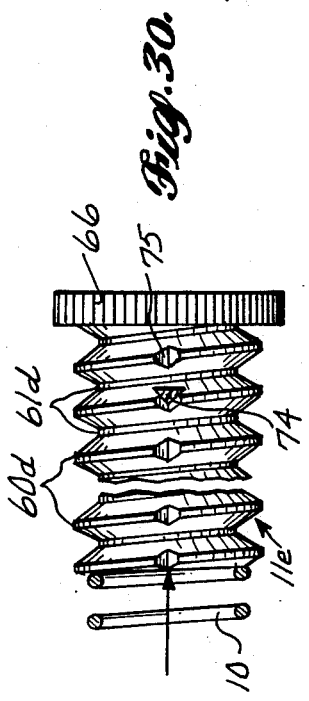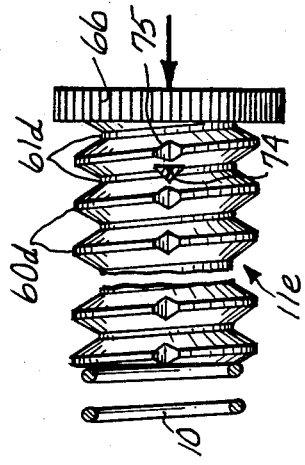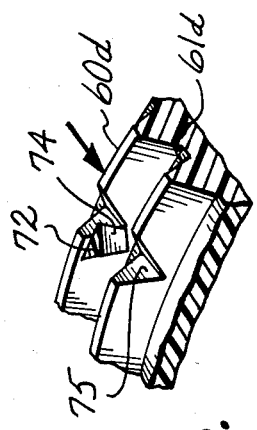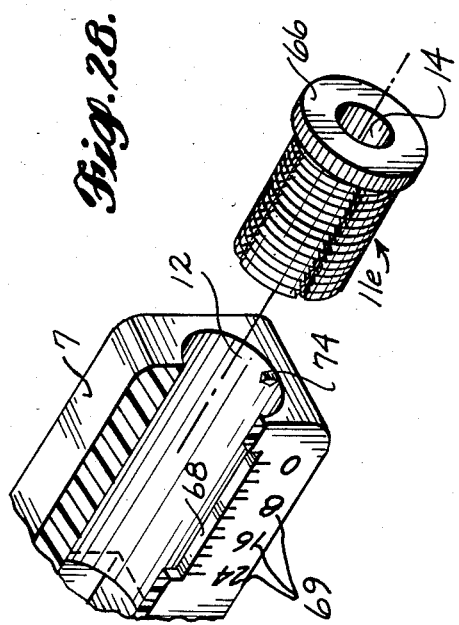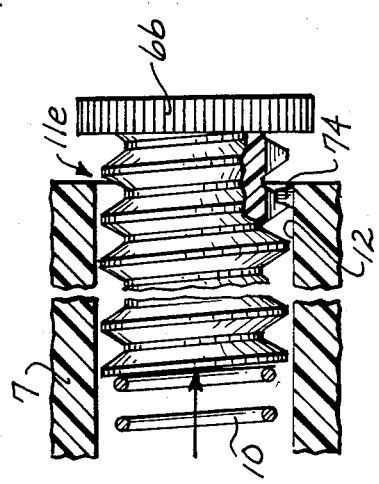

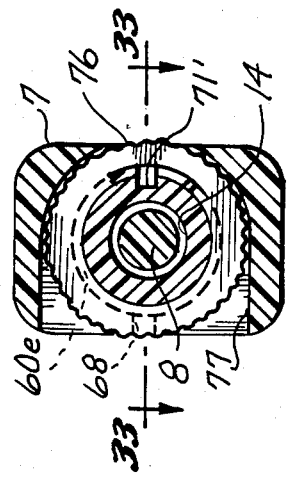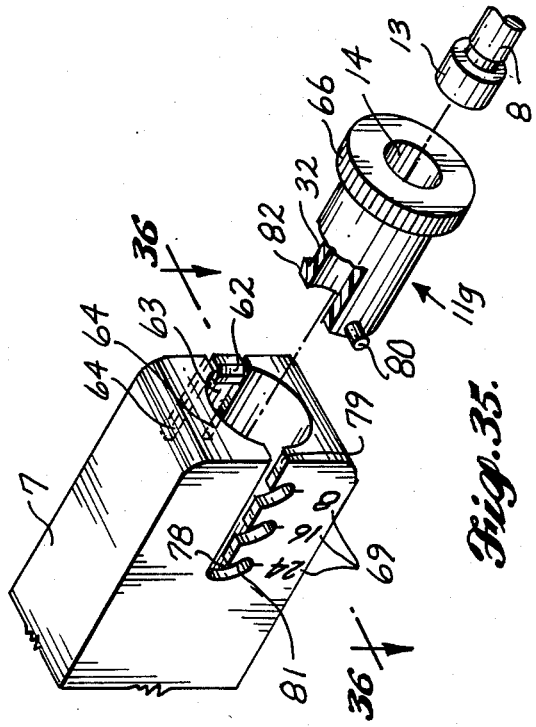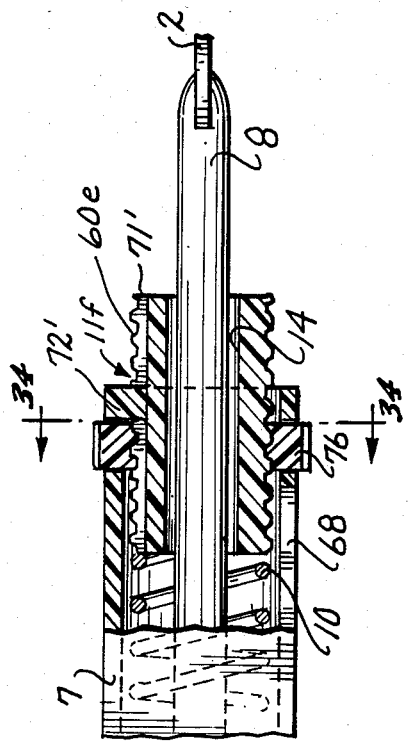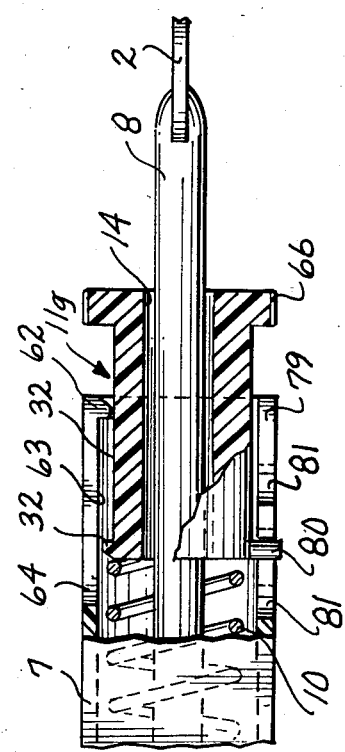

FORCE-ADJUSTABLE AND DISCONNECTIBLE CONNECTOR FOR ORTHODONTIC HEADGEAR

CROSS REFERENCE

This patent application is a continuation-in-part of our copending patent application Ser. No. 573,100, filed Jan. 23, 1984, for Force-Adjustable and Disconnectible Connector for Orthodontic Headgear.

BACKGROUND OF THE INVENTION

1. Field of the Invention

This invention relates to orthodontic headgear, and more particularly to a connector for exerting extraoral force from such headgear to the jaw of the wearer, which connector can be adjusted to provide extraoral force of different degrees and which connector is disconnectible if a force exceeding a predetermined force is exerted on it.

2. Prior Art

Armstrong U.S. Pat. No. 3,526,035, issued Sept. 1, 1970, discloses an orthodontic headgear including a spring which produces an extraoral force the degree of which force is indicated by calibrations.

Later Armstrong U.S. Pat. Nos. 4,115,921, issued Sept. 26, 1978, and 4,155,161, issued May 22, 1979, show extraoral headgears for producing an extraoral force including connectors which are disconnectible when a force exceeding a predetermined force is exerted on them.

Klein U.S. Pat. No. 4,226,589, issued Oct. 7, 1980, discloses a disconnectible orthodontic headgear connector including a return bent spring clip forming a disconnectible connection. The force exerted by such connector is produced by an elastic band or a spring of cross-leg type, which is unsatisfactory. Moreover, the travel of the disconnectible parts prior to disconnection is excessive, the minimum force which will effect disconnection is difficult to establish precisely, and the value of such force cannot be altered.

The still later Armstrong U.S. Pat. No. 4,238,188, issued Dec. 9, 1980, discloses a disconnectible connector employing a compression spring for producing an orthodontic force with means for adjusting such force and with a disconnectible connection, but such device is of considerable length.

Armstrong U.S. Pat. Nos. 4,368,039, issued Jan. 11, 1983, and 4,416,625, issued Nov. 22, 1983, which resulted from a continuation-in-part application of the application maturing into U.S. Pat. No. 4,368,039, disclose a different type of mechanism for adjusting the extraoral force produced by an orthodontic headgear connector.

Also a disconnectible connector incorporating a helical compression spring is shown in the publication High-Pull Traction Release System of Unitek Corporation bearing the copyright notice date of 1979.

SUMMARY OF THE INVENTION

A principal object of the present invention is to provide a connection for orthodontic headgear having some components corresponding to generally similar components embodied in prior orthodontic headgear connectors such as shown in the patents referred to above, namely, spring mechanism for producing an extraoral force, indicating means for indicating the force being exerted, means to adjust the degree of force produced by the force-producing mechanism and disconnectible mechanism for effecting disconnection of the connector by exertion on the connector of a force greater than a predetermined force, while at the same time making the connector compact, neat in appearance and precise in operation.

It is also an object to provide such a connector in which the working mechanism will be concealed to as great an extent as possible and which can prevent access to such working mechanism so as to be tamperproof.

Another object is to provide adjusting mechanism by which the force produced by the connector can be altered easily, quickly and reliably to enable the orthodontic headgear to exert different degrees of extraoral force on the jaw of the wearer.

The foregoing objects can be accomplished by a connector having a casing which houses a helical compression spring that exerts an extraoral traction force on a plunger. An abutment against which one end of the spring bears can be shifted axially of the spring relative to the casing to alter the length of the spring stroke available. A return bent spring clip that can be arranged to clamp one end portion of the casing will be pulled away from the casing by exertion on the connector of a force exceeding a predetermined force

BRIEF DESCRIPTION OF THE DRAWINGS

FIG. 1 is a top perspective of an orthodontic headcap including two connectors of the present invention.

FIG. 2 is a side elevation of one form of a connector according to the present invention.

FIG. 3 is a longitudinal section through the connector of FIG. 2 on an enlarged scale, and FIG. 4 is a similar section showing parts in different positions.

FIG. 5 is a top perspective of the connector showing components in exploded relationship and with parts broken away, and FIG. 6 is a similar top perspective with certain components shown in assembled relationship and other components shown in exploded relationship, parts being broken away.

FIG. 7 is a top perspective of the connector with more components shown in assembled relationship but having parts broken away.

FIG. 8 is a transverse section taken on line 8—8 of FIG. 3, and FIG. 9 is a similar section but showing components in a different relationship.

FIG. 10 is an enlarged fragmentary section similar to FIG. 3 but showing components in a different relationship, and FIG. 11 is a similar fragmentary section showing components in still a different relationship.

FIG. 12 is a top perspective of the connector turned end-for-end from FIG. 7, having parts broken away and illustrating one component in exploded relationship.

FIG. 13 is a top perspective of a modified form of the connector showing parts in exploded relationship.

FIG. 14 is a top perspective of a modified component of the connector, shown in exploded relationship with respect to another component of the headgear.

FIG. 15 is a top perspective of another modified component of the headgear, and FIG. 16 is a plan of the connector incorporating the modified component shown in FIG. 15.

FIG. 17 is a fragmentary top perspective of a portion of the connector shown generally in FIGS. 3 to 12, but having a different type of component which is adjustable longitudinally of the connector, parts being shown in exploded relationship and parts being broken away.

FIG. 18 is a more enlarged fragmentary longitudinal section of a portion of the connector shown in FIG. 17.

FIG. 19 is a fragmentary top perspective of a portion of a connector generally of the type shown in FIGS. 3 to 12, but having still a different type of component adjustable longitudinally of the connector, parts being shown in exploded relationship and parts being broken away.

FIG. 20 is a more enlarged detail longitudinal section through the portion of the connector shown in FIG. 19.

FIG. 21 is a fragmentary top perspective of a portion of a connector generally of the type shown in FIGS. 3 to 12, but having still another form of component adjustable longitudinally of the connector, and FIG. 22 is a more enlarged detail longitudinal section through a portion of the connector shown in FIG. 21.

FIG. 23 is a fragmentary top perspective of a portion of a connector generally of the type shown in FIGS. 3 to 12, but having still a different type of component adjustable longitudinally of the connector, parts being shown in exploded relationship and parts being broken away.

FIG. 24 is a detail longitudinal horizontal section through a portion of the connector shown in FIG. 23.

FIG. 25 is an end elevation on an enlarged scale of the connector shown in FIGS. 23 and 24 viewed from line 25—25 of FIG. 24 and having parts broken away.

FIG. 26 is a longitudinal section through a portion of a connector like that shown in FIG. 24 but having a slightly modified casing, and FIG. 27 is an end elevation of this connector on an enlarged scale viewed from line 27—27 of FIG. 26, parts being broken away.

FIG. 28 is a fragmentary top perspective of a portion of a connector generally of the type shown in FIGS. 3 to 12, but having a different type of component adjustable longitudinally of the connector, parts being shown in exploded relationship and parts being broken away.

FIG. 29 is an enlarged fragmentary longitudinal section of a portion of the connector shown in FIG. 28.

FIGS. 30 and 31 are fragmentary side elevations of a portion of the longitudinally adjustable components shown in FIG. 29, with parts shown in different relative positions.

FIG. 32 is a top perspective of a fragment of the longitudinally adjustable component shown in FIG. 31 on an enlarged scale with parts in the relative positions shown in FIG. 31.

FIG. 33 is a plan of a portion of a different form of connector with parts broken away along line 33—33 of FIG. 34, and FIG. 34 is a transverse section through the connector taken on line 34—34 of FIG. 33.

FIG. 35 is a fragmentary top perspective of a portion of still another form of connector with parts in exploded relationship and having parts broken away.

FIG. 36 is a plan of the portion of the connector shown in FIG. 35 with parts broken away along line 36—36 of FIG. 35.

DETAILED DESCRIPTION

Two connectors according to the present invention can be connected between opposite sides, respectively, of an orthodontic headgear headcap 1 made of nonstretchable fabric or webbing and side straps 2 made of flexible nonstretchable plastic having apertures 3 at regularly spaced intervals along their lengths for engagement with hooks on opposite ends of an orthodontic facebow or chin cup. The straps are connected to a face bow or chin cup for applying force of a spring in the connector to the wearer's jaw and the headcap or a neckband applies a reaction force to the wearer's head. The cheeks of the wearer can be protected from contact by the connectors 4 by tabs 5 of webbing having one end anchored by a staple 6 or by sewing to a side of the headcap and projecting from the headcap downward and forward along the side of the wearer's head.

The connector includes principally an elongated casing 7 made of suitable plastic material such as nylon within which a plunger reciprocates to exert force on the strap 2. The plunger includes a rod 8 having on its end remote from the strap 2 a composite head 9. The force-producing helical compression spring 10 is engaged between such head and the end of a spring-abutment generally cylindrical member shown as sleeve 11 which is adjacent to the spring when the connector is assembled. Such sleeve is lodged in an aperture 12 in the end of 5 casing 7 adjacent to strap 2.

The composite plunger head 9 includes a knob 13 on the end of rod 8 remote from strap 2 which is of a size to slide in close-fitting relationship through the bore 14 of sleeve 11. Such knob can be coupled with a boss 15 of a slide 16 by being moved transversely of the length of rod 8 into a socket 17 within such boss through a side opening gate. The end of the cavity in boss 15 remote from slide 16 has an internal flange 18, the inner edge of which fits into the neck 19 formed as an annular groove in rod 8 at the base of knob 13. Such flange can enter the neck groove because of the gate 20 in such flange in registration with the lateral opening into socket 17 of boss 15.

The knob 13 is retained in the socket 17 of boss 15 by a keeper collar 21 having a bore of a size to fit slidably over the boss. The end of such collar remote from the slide 16 has an internal flange 22 with an aperture of a size to fit slidably over the knob 13. A lug 23 projecting inwardly from the interior of the collar adjacent to flange 22 is of an axial width corresponding to the thickness of flange 18 of boss 15 and of a circumferential extent corresponding to the gate 20 of such flange.

In assembling the components of the connector from their exploded relationship shown in FIG. 5 to their partially assembled relationship shown in FIG. 6, the knob 13 of the stem 8 is first inserted through the bore 14 of sleeve 11 and then through end aperture 12 of casing 7. At such time the sleeve 11 may or may not have been installed in the aperture 12 of casing 7 depending on the length of the rod 8.

Next compression spring 10 is slid over the knob 13 and that portion of the rod 8 projecting beyond the end of sleeve 11 remote from the strap 2. The flange 22 of collar 21 will then be slid over the knob 13 compressing spring 10 between collar 21 and spring-abutment sleeve 11 as necessary to enable the knob to project beyond the end of casing 7 remote from its aperture 12. In that position, the boss 15 of slide 16 can be moved transversely of the length of rod 8 to slide the boss over the knob so that it is lodged in cavity 17 of the boss and flange 18 is fitted into the neck groove 19 of the rod. The force-compressing spring 10 can then be relieved to enable such spring bearing on flange 22 of collar 21 to slide such collar over boss 15 of slide 16 and move lug 23 into the gate 20 of flange 18.

With the internal components of the connector thus assembled, sleeve 11 is fitted into aperture 12 of casing 7 if it is not already in such position. Strap 2 can then be pulled so that the composite head 9 of the plunger composed of knob 13, slide 16 and collar 21 can be urged against the adjacent end of compression spring 10, the opposite end of which abuts the adjacent end of sleeve 11, until the end of slide 16 begins to enter the open end of casing 7. During such manipulation, the noncylindrical slide 16, which is of generally square profile, will be rotatively oriented to fit the open end of the casing. In such position a lug 24 projecting from one side of the slide and tapered toward the casing will engage a tongue 25 having in it a slot 26 elongated lengthwise of the elongated casing 7 and parallel to the rod 8. The tongue is made of the same resilient material as the casing, such as hard plastic, and is formed between parallel blind or open-ended slots 27 in the casing wall at opposite sides of the tongue so that such tongue extends in cantilever fashion toward the open end of casing 7.

As the strap 2 is pulled to draw slide 16 into the open end of casing 7, the tapered lug 24 will wedge the flexible tongue 25 outwardly until such lug comes into registration with the slot 26, whereupon the tongue will snap back toward the cavity of the casing. The tongue 25 and lug 24 thus form a catch limiting movement of the slide outward from the cavity of the casing, constituting a snapback travel limit, which catch retains the internal components of the connector in their assembled relationship shown in FIG. 7.

The orthodontic force which will be exerted by spring 10 on strap 2 will depend upon the degree to which such spring is compressed between the flange 22 of the plunger rod 8 and the abutment face 28 of sleeve 11 engaged by one end of the spring, i.e. the effective length of the spring which in turn will depend upon the position of the sleeve longitudinally of casing 7 and the lengthwise relationship between the plunger head 9 and the casing.

When a pull is not being exerted on rod 8, the travel of the plunger head away from sleeve 11 will be limited by engagement of the catch lug or lugs 24 with the end of slot or slots 26 remote from the sleeve. The minimum force exerted by the spring can be regulated by establishing the relationship of sleeve 11 relative to the casing 7 longitudinally of the spring and rod 8. The construction of the connector enables the longitudinal position of the spring-abutment sleeve relative to the casing to be altered so as to be able to adjust selectively the minimum degree of force exerted by the spring when the rod is in such position relative to the casing.

To enable the degree of spring force applied to the headcap 1 and the strap 2 to be adjusted the force-setting abutment or sleeve 11 shown in FIGS. 3 to 12 has latch means including as a first component axially spaced annular flanges 29a, 29b, 29c and 29d perpendicular to the axis of the sleeve separated by axially spaced annular grooves. The groove 30a is located between adjacent flanges 29a and 29b, the groove 30b is located between adjacent flanges 29b and 29c and the groove 30c is located between adjacent flanges 29c and 29d.

The aperture 12 in the end of casing 7 in which the abutment or sleeve 11 is lodged is formed by an internal flange 31 of varying radial width constituting a second component of the latch means. The annular flanges 29b, 29c and 29d of the sleeve are not of full circular cross section, but are interrupted, their opposite sides being truncated to form diametrically opposite chordal surfaces 32. Correspondingly, casing aperture 12 is not circular but its diametrically opposite sides 33 are chordal complemental to the opposite sides of the sleeve flanges 29b, 29c and 29d. As shown in FIG. 8, therefore, when the sleeve 11 is turned into the proper rotative position relative to the noncircular casing aperture 12, the sleeve can slide outward through such aperture from the interior of the casing until opposite portions of the circular flange 29a engage the outer surface of casing flange 31 adjacent to the chordal flange portions 33. When the sleeve 11 has been moved axially relative to the casing to place a selected annular groove 30a, 30b or 30c in registration with a casing flange 31, the sleeve and casing may be turned relatively through an angle of 90 degrees to alter the relationship of the casing and sleeve from that shown in FIG. 8 to that shown in FIG. 9 for latching the sleeve to the casing.

The axial widths of grooves 30a, 30b and 30c are greater than the thickness of casing flange 31, and may be approximately twice as great as such flange thickness, so that sleeve 11 can be moved axially relative to casing 7 to a limited extent even when the sleeve and casing aperture 12 are in the relative positions shown in FIG. 9. To maintain the sleeve and casing in such relative rotative positions against inadvertent circumferential displacement teeth 34a, 34b and 34c are provided in the respective annular grooves 30a, 30b and 30c of sleeve 11. Such teeth project axially away from spring 10 into the grooves from the groove sides remote from strap 2 and adjacent to such spring. Such teeth preferably are tapered away from their roots and are of a profile complemental to the profile of a notch or notches 35 located in a chordal side, or both chordal sides, of the aperture 12 in casing flange 31. When the sleeve 11 is in the rotative position relative to casing 5 shown in FIG. 9, therefore, the tooth of the groove in which flange 31 is fitted will mesh with a notch 35. The force exerted by spring 10 against the end 28 of sleeve 11 will press the sleeve in a direction to maintain its tooth engaged with the flange notch to prevent relative rotation of the sleeve and casing.

One or both of the chordal surfaces 32 are labeled at the locations of the respective annular flanges 29b, 29c and 29d with designations 36 indicating the orthodontic force produced by compression spring 10 corresponding to the longitudinal position of sleeve 11 in casing aperture 12. FIG. 5 shows number 16 in registration with flange 29b, number 24 in registration with flange 29c and number 32 in registration with flange 29d. These numbers represent ounces of orthodontic force produced by the spring 10.

When the abutment or sleeve 11 is in the position relative to casing 7 shown in FIG. 10, the number 16 will be visible adjacent to the end of the casing, indicating that an orthodontic force of 16 ounces will be exerted on strap 2 when that strap is pulled so that the outer face of slide 16 is substantially flush with the adjacent end of casing 7, as shown in FIG. 10. When the sleeve 11 is adjusted axially relative to casing 7 to the position shown in FIG. 3 in which annular groove 30b is in registration with casing flange 31, the number 24 on chordal surface 32 will be seen adjacent to the end of casing 7. Such designation indicates that an orthodontic force of 24 ounces will be exerted when strap 2 is pulled so that the outer end of slide 16 is substantially flush with the adjacent end of the casing, as shown in FIG. 3. When the abutment or sleeve 11 has been adjusted longitudinally relative to the casing 7 to the position shown in FIG. 11, the number 32 on flange 29a will be visible adjacent to the apertured end of casing 7. With the sleeve in this position of adjustment, the orthodontic force produced when the strap is pulled sufficiently to place the outer end of slide 16 substantially flush with the open end of casing 7, as shown in FIG. 11, will be 32 ounces.

In order to exert an orthodontic force on a strap 2, it is necessary for casing 7 to be connected to a reaction member such as the headcap 1 or a neckstrap. For safety purposes, however, it is desirable to have the connection between the strap 2 and the headcap 1 be disconnectible if a pull greater than a predetermined force is exerted on a strap 2, for reasons discussed in detail in the Armstrong prior U.S. Pat. Nos. 4,115,921 and 4,155,161. Disconnection of the present connector is afforded by a clip 37 arranged to clamp casing 7, as shown best in FIGS. 2 and 3. Such clip is preferably made of resilient metal and includes a cross member 38 from opposite ends of which project generally parallel legs 39. The cross member can extend through a loop 40 of fabric or webbing carried by the headcap 1, or a neckstrap, which extends generally parallel to and overlaps the protective fabric tab 5, as shown in FIG. 2. To enable the attitude of the clip to be controlled more readily, its transverse member 38 may include a central loop handle 41 fitted between the parts of the fabric loop 40, as shown in FIG. 12.

The generally parallel clip legs 39 include clamping portions 42 offset toward each other and preferably disposed in parallel relationship when they are in clamping engagement with casing 7. Such clamping portions of the clip legs can engage in grooves 43 formed in the opposite sides of the casing. Such grooves include portions of a length equal to the length of the clip-clamping portions 42 so that there is no endwise play between the clip and the casing. Such slot portions have shoulders 44 at their ends closer to the adjacent end of the casing 7 and the offset clamping portions 42 of the clip legs 39 have converging leg portions 45 adjacent to them engageable with such shoulders. The tips 46 of the generally parallel clip legs are bent oppositely outward, as shown in FIGS. 3 and 4.

The slide 16 is slidable snugly in the cavity 47 formed by the open end of the casing 7. Inward movement of such slide is limited to the position shown in FIG. 4 by engagement of the inner end of such slide with a circumferential shoulder 48 in the casing cavity. Travel of the plunger lengthwise of rod 8 is therefore limited in one direction by engagement of a lug 24 with the end closer to the adjacent end of the casing of a slot 26 in which it is engaged and in the opposite direction by engagement of the inner end of slide 16 with casing shoulder 48.

Increasing the pull on strap 2 relative to casing 7 will draw rod 8 progressively out of the casing until the inner end of slide 16 bottoms on shoulder 48. Such engagement will terminate travel of rod 8 outward of the casing. If the pull on strap 2 continues to increase, the force between shoulders 44 and the convergent portions 45 of the legs of clip 37 will wedge the clip legs apart until the casing-engaging portions 42 slide over the casing shoulders 44, as shown in FIG. 4. Such movement will effect disconnection of the clip from the casing.

Separating movement of the clip legs from the attitude of FIG. 3 to the attitude of FIG. 4 is very small because the casing shoulders 44 are rather abrupt and not very high. Consequently, the clip will maintain its position shown in FIG. 3 until the predetermined limiting force has been reached, whereupon the clip legs will be wedged apart to the attitude shown in FIG. 4 instantaneously and disconnection will occur with virtually no possibility of the resilience of the clip restoring its legs to the positions of FIG. 3 once they have been wedged apart appreciably. To reconnect the clip with the connector body 7, it is merely necessary to push the outturned tips 46 into the casing grooves 43 in the manner illustrated in FIG. 12, whereupon the tips will wedge the clip legs apart so that they can enter their respective grooves 43 and restore the connector to its connected condition shown in FIG. 3.

The amount of pulling force on strap 2 that can be tolerated before the connector will disconnect depends on the clamping force exerted by the clip 37 on the connector casing 7. Such clamping force can be determined by the selection of the material of the clip 37 as to type of metal, cross-sectional size of the clip stock and tempering of the metal.

It is possible to disassemble the components of the connector described above by wedging outward the free ends of tongues 25 until the catch lugs 24 are freed from slots 26. A connector which is tamperproof can be provided by enclosing the working parts of the connector in a sealed casing 7' as incorporated in the modified connector shown in FIG. 13. The working components of this connector are substantially identical to those described in connection with FIGS. 3 to 12 but, in this instance, the casing 7' is formed of two complemental halves 49a and 49b. Instead of the casing being open at the end opposite the aperture 12, such end is closed by cooperating end wall sections 50a and 50b. The working mechanism can be assembled outside of the casing and then the casing halves assembled over it so that the slide 16 will be received half in the casing cavity 47a and the other half in the casing cavity 47b.

Registration of the casing halves in assembling them will be ensured by peg 51a in one corner of section 49a fitting in socket 51b of the corresponding corner of section 49b; socket 52a in another corner of section 49a fitting over peg 52b in the corresponding corner of section 49b; peg 53a in another corner of section 49a fitting into socket 53b in a corresponding corner of section 49b; and socket 54a in the other corner of section 49a fitting peg 54b in the corresponding corner of section 49b. A suitable adhesive can be used to bond together the matching edges of the two casing sections 49a and 49b to prevent their disassembly.

While not shown in FIG. 13, each of the casing sections 49a and 49b would have in the outer sides of their end portions enclosing the slide 16 grooves 43 such as shown in FIGS. 3 to 7 and 10 to 12 for the purpose of receiving parallel legs 42 of a clip 37, which would resiliently grip the casing between them as long as the connector is not subjected to excessive tension force. The action of such connection would be the same as described with respect to the connector shown in FIGS. 3 to 12.

The head 9 of the rod 8 in FIG. 13 could be made in a single piece if the rod 8 and strap were made separately and connected by a joint such as illustrated in FIG. 14. The end of rod 8 remote from head 9 or knob 13 has an end portion 8' of reduced width carrying a button or headed pin 8'' that can be forced through the end opening 3'' of a side strap 2' having additional spaced apertures 3' arranged along its length. The button or headed pin and aperture 3'' preferably are constructed so that the parts can be disassembled without mutilating either the button or the buttonhole, but these components should be connected sufficiently securely so that they will not become separated inadvertently.

In order to minimize cocking of the connector casing 7 where the loop 40 is provided in a neckstrap, the clip may have an offset cross member of the type shown in FIGS. 15 and 16. The generally parallel legs of the clip may be like those described in connection with FIGS. 3 and 4 including parts 39 from which sections 45 converge inwardly to the casing clamping portions 42 that have outturned tips 46. Instead of the leg sections 39 being connected directly by a cross member, however, offsetting sections 55 connect the sections 39, respectively, to the opposite ends of a cross member 38'. Such cross member is not shown as having a handle loop such as 41, but it could be provided with such a handle loop if desired.

The length of offsetting sections 55 is equal to approximately one-half the thickness of the casing 7, as shown in FIG. 16, so that when the connecting section 38' is received in webbing loop 40 and the clip and casing are in assembled relationship, the loop and casing will not be cocked appreciably even though the casing grooves in which the clip legs are engaged are located substantially in the center of the casing and parallel to the opposite sides of the casing.

As explained above, the force that compression spring 10 exerts on rod 8, and consequently on strap 2, depends on the degree to which such spring is compressed when the end of slide 16 is flush with the adjacent end of casing 7 as shown in FIGS. 3, 10 and 11. The initial compression of the spring can be altered by shifting the abutment or sleeve 11 longitudinally of the casing. When the sleeve is shifted inwardly, the initial degree of compression of spring 10 is increased so that the force exerted on strap 2 will be greater. Conversely, if the sleeve is moved outward relative to casing 7, the initial degree of compression of the spring will be reduced so that the force which it produces on strap 2 will be decreased.

The longitudinal position of a spring-engaging abutment or sleeve can be altered and fixed relative to casing 7 in various ways in addition to that illustrated in FIGS. 3, 10 and 11, and a variety of other structures to accomplish such function is illustrated in FIGS. 17 to 36.

The sleeve 11a shown in FIGS. 17 and 18 is similar to the sleeve 11 shown in FIGS. 3 to 13, except that instead of the annular flanges 60 perpendicular to the axis of the sleeve being interrupted by chordal surfaces they are circumferentially continuous. Similarly, the annular grooves 61 between the flanges are circumferentially continuous. The aperture 12 in the end of casing 7 is circular to enable the sleeve 11a to slide longitudinally through such aperture. Such movement of the sleeve can be arrested in any of several positions of longitudinal adjustment, such as corresponding to the positions of FIGS. 10, 3 or 11, by providing a resilient catch having a square tooth or pawl 62 that can lodge in the appropriate groove 61 corresponding to the desired longitudinal position of the sleeve. FIG. 18 shows the tooth lodged in the middle groove 61 of the sleeve corresponding to the position of the sleeve 11 in FIG. 3.

The tooth 62 is carried by and projects inward from a spring leaf 63 made of the same plastic material as the casing 7. This spring leaf is of the cantilever type formed by providing parallel open-ended or blind slots 64 extending inward from the end of the casing 7 adjacent to the aperture 12, as shown in FIG. 17. The resilient leaf 63 preferably has a tab 65 projecting from its free end beyond the tooth 62 which can be grasped to swing the leaf from the solid line position outward to the broken line position shown in FIG. 18 and thereby withdraw the tooth from a groove 61 so that the sleeve 11a can be slid longitudinally inward or outward relative to casing 7 through aperture 12.

In order to prevent the force produced by spring 10 from being greater than desired, it is preferred that the outer end of sleeve 11a have a full, or at least a partial, radially-projecting end flange 66 of somewhat larger diameter than the flanges 60 so as to abut the exterior margin of the casing aperture 12 when the sleeve is pushed fully in and thereby limit such inward movement. Such end flange may have one or more notches 67 large enough to accommodate the tab 65 of leaf 63 so that the end flange 66 can be moved fully into abutment with the end of the casing.

To be able to determine easily the force that spring 10 would exert on a strap 2 for different adjusted positions of an abutment or sleeve 11a lengthwise of the casing 7, a slot 68 extending lengthwise of the casing can be provided through which the inner end of the abutment or sleeve can be seen. Numbers 69 can be arranged along the slot, indicating the force that would be produced by the spring when the inner end of the sleeve is in registration with an index mark corresponding to a number indicating a particular force value. The numbers 69 range from 12 ounces to 32 ounces of spring force.

In FIGS. 19 and 20 the exterior of the sleeve 11b is cylindrical except for two longitudinal grooves. One of these grooves is a rack groove 70 having ratchet teeth 60a upstanding from its bottom forming inwardly tapered notches 61a between the teeth. A pawl or latch tooth 62a carried by and projecting inward from the end of a resilient leaf 63 can engage in the notches 61a as shown in FIG. 20. The leaf 63 is of the type described in connection with FIGS. 16, 17 and 18 formed by parallel blind or opening grooves 64 in a side of the casing.

The inner side of the tooth 62a is abrupt for abutment with the vertical faces of the buttress teeth 60a in rack groove 70 to latch the sleeve 11b in a selected, longitudinally adjusted position as shown in FIG. 20. The outer side of the tooth or pawl 62a is inclined generally complemental to the inclined sides of the rack teeth 60a so as to form a ratchet enabling the sleeve 11b to be shifted inwardly relative to the casing 7 by simply pushing on the outer end of the sleeve. Inward movement of the sleeve is limited by engagement of the sleeve end external radial flange 66 with the end of the casing 7. In this instance also the flange 66 has at least one notch 67 to receive the tab 65 projecting from the end of the leaf 63 beyond the tooth 62a, which can be grasped for lifting the leaf end to retract the tooth 62a out of the path of ratchet teeth 60a so that the sleeve can be moved outward by the pressure of spring 10 against its inner end.

In order to retain sleeve 11b in a position circumferentially so that the rack teeth 60a will be in registration with the pawl or tooth 62a, a longitudinal groove 71 is provided in the circumference of the sleeve which is circumferentially offset from rack groove 70 and is engageable with a projection 72 projecting radially inward from the periphery of the aperture 12 and of a width to fit into the groove 71.

The casing 7 in FIG. 20 also has a longitudinal slot 68 through which the inner end of sleeve 11b can be viewed for correlation with index marks corresponding to the various numbers 69 for indicating the force that will be produced by spring 10 when the sleeve is in various adjusted positions.

In the structure shown in FIGS. 21 and 22 relative turning of the sleeve 11c and the casing 7 is prevented by making the casing aperture 12' and the cross section of sleeve 11c of complemental noncircular shape, such as being approximately square, instead of utilizing interengagement of a projection 72 in a groove 71 such as described in connection with FIGS. 19 and 20.

This connector also has a longitudinal rack slot 70', but the rack teeth 60b are of the vee type rather than being buttress teeth as in the rack groove structure shown in FIGS. 19 and 20. A tooth 62b having opposite sides inclined equally can fit into grooves 61b of complemental shape between the teeth 60b. Such tooth is carried by the end of a resilient cantilever tongue 63 of the type described in connection with FIGS. 17 to 21. Preferably the inclination of the opposite sides of tooth 62b is sufficiently great that the sleeve 11c can be shifted either inward or outward relative to the casing 7 by application of longitudinal force to the sleeve while the tooth 62b and the rack in groove 70' function as a ratchet.

The outer end of sleeve 11c has a flange 66' engageable with the end of casing 7 to limit inward movement of the sleeve and which can be grasped to pull the sleeve outward. Such flange has in it a notch 67' to accommodate tab 65 projecting from leaf 63 when the slide is in its fully retracted position. Also the casing 7 has in its side opposite the leaf 63 a slot 68 for viewing the inner end of sleeve 11c, the position of which can be designated by numbers 69 arranged along the length of slot 68 corresponding to different degrees of spring force.

The sleeve 11d of the connector shown in FIGS. 23 to 27, inclusive, has an external square helical thread instead of circumferential flanges perpendicular to the axis of the sleeve such as provided on the sleeves of FIGS. 3 to 12, 17 and 18. The square thread includes the raised portions 60c and the intervening grooves 61c. Also the threads are truncated to form diametrically opposite chordal surfaces 32 as in the sleeve of FIGS. 5 to 9 and 12. In this construction relative turning of the sleeve and casing 7 is prevented by the lug or projection 62 bearing on a flat chordal surface 32 of the sleeve. While a larger or smaller number of such chordal surfaces might be provided, two such surfaces are shown on the sleeve of FIGS. 23 to 27, enabling the sleeve to be held relative to the casing in either of two positions turned 180°.

With a sleeve construction of the type shown in FIGS. 23 to 27, the sleeve is moved longitudinally of the casing 7 by turning the sleeve relative to the casing. Longitudinal movement is accomplished by providing a tooth 73 projecting radially inward in the casing aperture 12, which projects into the thread groove 61c. The amount of adjustment of the sleeve longitudinally of casing 7 for a given degree of sleeve rotation will depend on the pitch of the thread. The projection 62 may be arranged so that intentional rotation of the sleeve will cause a thread projection 60c to bear against the projection and wedge it outward so that it will ride on the crests of thread portions 60c until the sleeve has been turned to bring the next chordal surface 32 into registration with the projection 62.

It is preferred that the outer end of sleeve 11d have a knurled external radial flange 66 larger than the threads 60c that can be grasped to facilitate turning of the sleeve relative to the casing. In order to enable the sleeve to be moved into the casing to its fullest extent so that the flange abuts the end of the casing, a notch 67 is provided in the flange at an appropriate location to receive the tab 65 of the resilient leaf 63 when the sleeve is in its farthest inward position.

In the type of connector shown in FIGS. 23, 24 and 25 two tooth projections 73 are provided in diametrically opposite positions so that when the sleeve 11d is turned to place the chordal surfaces 32 in registration with the projections 73 and the pawl 62 is withdrawn to the broken line position shown in FIG. 25, the sleeve can be slid longitudinally of the casing as described in connection with FIGS. 17 and 18. When the sleeve has been set to the desired adjusted position, it can be turned 90° and the tab 65 released so that the pawl will engage a chordal surface 32 to hold the sleeve against rotation relative to the casing in such adjusted position.

In the connector structure shown in FIGS. 26 and 27 three projections 73' project inward from the aperture 12 so that at least two of the projections are always engaged with a thread groove. With such a construction the only way that the sleeve can be moved longitudinally of the casing 7 is by rotation of the sleeve relative to the casing. When the desired longitudinal adjustment has been accomplished, the resilient leaf 63 is released so that its projection 62 will bear on a chordal surface 32 to prevent further inadvertent relative rotation of the sleeve and casing.

The sleeve 11e shown in FIGS. 28 to 32 that is adjustable longitudinally relative to casing 7 has a helical external thread, but instead of the thread being of the square type as shown in FIGS. 23 to 27 it is a vee type thread having projections 60d with outwardly converging sides and intermediate grooves 61d with outwardly flaring sides. The sleeve 11e can be adjusted longitudinally relative to the casing only by being rotated relative to the casing, because the outwardly tapered projection 74 projecting outward from the casing aperture 12 is engaged in the helical groove 61d. The outer end of the sleeve preferably has a knurled external radial flange 66 larger than the thread 60d which can be grasped to rotate the sleeve.

The position of sleeve 11e lengthwise of the casing 7 can be adjusted in small increments by providing on the thread latch means for cooperation with the projection 74. Such latch means includes circumferentially-spaced notches 75 in the crests of the thread. The projection is tapered away from the adjacent end of the casing to a ridge generally complemental to the shape of the thread notches 75 so as to latch the sleeve securely against inadvertent rotation relative to the casing by interengagement of the projection with a thread notch. Such interengagement is maintained by the longitudinal pressure on the sleeve effected by the spring 10 in the direction indicated by the arrow in FIG. 30.

To release the latch means for enabling rotation of the sleeve relative to the casing, the sleeve may be shifted slightly in the direction indicated by the arrow shown in FIG. 31 in opposition to the pressure of spring 10 so that the projection 74 is in registration with the grooved portion 61d of the thread. The projection and notches may, however, be shaped so that intentional rotation of the sleeve will cause the projection to wedge against an edge of a thread notch and thereby move the sleeve longitudinally relative to the casing sufficiently so that the projection will escape from the thread notch and enable the sleeve to be turned to the position in which the next notch of the sleeve will engage with the projection. Such notches are shown in FIG. 28 as being spaced apart 90° circumferentially, but finer longitudinal adjustment could be obtained by placing the notches closer together or by decreasing the pitch of the thread.

The connector shown in FIGS. 28 to 32 has a longitudinal slot 68 in its wall through which the inner end of the sleeve 11e may be seen, as explained in connection with other figures, to enable the numbers 69 to indicate the degree of force being produced by the spring 10 for the particular position of the sleeve adjusted longitudinally of the casing.

FIGS. 33 and 34 show a different type of threaded construction for adjusting the sleeve 11f longitudinally relative to the casing 7. In this construction the sleeve has an external thread 60e that is engageable by a nut 76 fitted in a side opening recess 77 in the casing. The nut is large enough so that its diametrically opposite sides project beyond opposite sides of the casing 7 as shown in FIGS. 33 and 34. The circumference of the nut preferably is knurled so as to facilitate turning of the nut relative to the casing by thumb-and-finger engagement of its diametrically opposite sides.

The rod 8 extends through the bore 14 of the sleeve and the helical spring 10, the adjacent end of which abuts the inner end of the sleeve. Pressure of the spring on the sleeve will be transmitted to the nut 76 to press its side adjacent to the end of the casing against the end of the recess 77 nearer the casing end to provide frictional contact which will deter inadvertent rotation of the nut relative to the casing.

Rotation of the nut 76 relative to the casing in one direction will move sleeve 11f longitudinally inwardly of the casing to increase the force of spring 10, whereas rotation of the nut relative to the casing in the opposite direction will move the sleeve longitudinally outward to decrease the force of spring 10. Inadvertent rotation of sleeve 11f relative to the casing 7 by rotation of nut 76 will be prevented by projection 72' projecting inward from casing 7 engaging in a longitudinal groove 71' in the sleeve 11f.

The effect on the force of spring 10 produced by the adjustment of sleeve 11f relative to the casing 7 can be determined by viewing the inner end of the sleeve through a longitudinal slot 68 in the casing as discussed previously. Appropriate numbers can be arranged along the slot to indicate the amount of spring force, as discussed in connection with FIGS. 17 and 18, for example. Fine graduations between numbers indicating the force in ounces can be provided along the margin of groove 68 as shown in FIG. 28.

Still a different type of construction for enabling the longitudinal position of an abutment sleeve to be established relative to the casing is illustrated in FIGS. 35 and 36. In this instance the sleeve 11g is cylindrical except for a flat chordal portion 32 or reduced arcuate portion on one side and the knurled external radial flange 66 on the outer end of the sleeve.

In this construction, instead of the casing having a slot with closed ends, such as the slot 68 shown in FIGS. 17, 19 and 23, a longitudinal slot 78 is provided in one side of the casing 7 that has an end opening 79. A pin or lug 80 projecting laterally outward from the inner end portion of sleeve 11g can be inserted into the open end 79 of slot 78, and the sleeve can simply be shifted longitudinally of the casing into approximately the desired position adjusted longitudinally of the casing to afford the proper compression of spring 10 and hence the force produced by it. The sleeve can be retained in such a selected longitudinally adjusted position by being rotated slightly in the counterclockwise direction as seen in FIG. 35, which will move pin 80 circumferentially into a selected one of the notches 81 communicating with the slot 78 to form bayonet slots. As shown in FIG. 35, numbers 69 are provided adjacent to such notches to indicate a spring force of eight ounces, sixteen ounces and twenty-four ounces, respectively. The notches 81 preferably are inclined somewhat from the slot 78 to their bottoms in a direction away from spring 10 and toward the adjacent end of casing 7 so that the pin 80 will be lodged securely in a particular notch selected.

It is preferred that provision be made for retaining the sleeve 11g and the casing 7 in assembled relationship. Such result can be accomplished by providing a projection 62 carried by a spring leaf 63 formed of casing material by parallel open-ended slots 54 as described in connection with FIGS. 17 to 22, for example. The side of sleeve 11g opposite pin 80 has a chordal or reduced arcuate surface 32' into which the lug 62 can fit. Preferably the chordal or reduced arcuate portion of the sleeve does not extend completely to its inner end but stops short of the sleeve end to provide a radial projection 82 engageable by lug 62 to limit outward movement of the sleeve.

It is preferred that the surface of projection 82 adjacent to the inner end of the sleeve and the outer surface of casing projection 62 be inclined generally complementally so that forcing the sleeve projection 82 against lug 62 in the direction to insert the sleeve into the casing end will wedge the leaf 63 outward until the projection 82 passes the lug 62. The resilient leaf will then snap back to the position shown in FIG. 36 in which the lug 62 will be engaged by sleeve projection 82 as the sleeve is moved outward to limit such outward movement of the sleeve. The sleeve can be removed from the casing, if necessary, however, by wedging the lug 62 outward sufficiently to enable projection 82 to move past it as the sleeve is moved farther outward.

We claim:

1. A force-producing connector for orthodontic headgear including force-reaction means engageable with the head or neck of a wearer, force-applying means for applying force to the wearer's jaw, a helical compression spring, means for applying force produced by the spring to the force-reaction means and the force-applying means, a casing, abutment means engageable by the spring and carried by the casing and interengageable means for holding the abutment means relative to the casing in different positions axially of the spring to alter the effective spring length and consequently the force produced by the spring on the force-reaction means and the force-applying means, the improvement comprising the interengageable means having spaced projections on the abutment means which form grooves between adjacent projections, said grooves constituting socket means, and projection means engageable in said socket means.

2. The connector defined in claim 1, in which the spaced projections are flanges of square cross section.

3. A force-producing connector for orthodontic headgear including force-reaction means engageable with the head or neck of a wearer, force-applying means for applying force to the wearer's jaw, a helical compression spring, means for applying force produced by the spring to the force-reaction means and the force-applying means, a casing, abutment means engageable by the spring and carried by the casing and interengageable means for holding the abutment means relative to the casing in different positions axially of the spring to alter the effective spring length and consequently the force produced by the spring on the force-reaction means and the force-applying means, the improvement comprising the interengageable means having socket means including a tooth rack and projection means engageable with said socket means.

4. The connector defined in claim 3, in which the projection means includes a pawl engageable with the tooth rack for forming a ratchet.

5. A force-producing connector for orthodontic headgear including force-reaction means engageable with the head or neck of a wearer, force-applying means for applying force to the wearer's jaw, a helical compression spring, means for applying force produced by the spring to the force-reaction means and the force-applying means, a casing, abutment means engageable by the spring and carried by the casing and interengageable means for holding the abutment means relative to the casing in different positions axially of the spring to alter the effective spring length and consequently the force produced by the spring on the force-reaction means and the force-applying means, the improvement comprising the interengageable means having socket means including a buttress tooth rack and projection means engageable with said socket means.

6. A force-producing connector for orthodontic headgear including force-reaction means engageable with the head or neck of a wearer, force-applying means for applying force to the wearer's jaw, a helical compression spring, means for applying force produced by the spring to the force-reaction means and the force-applying means, a casing, abutment means engageable by the spring and carried by the casing and interengageable means for holding the abutment means relative to the casing in different positions axially of the spring to alter the effective spring length and consequently the force produced by the spring on the force-reaction means and the force-applying means, the improvement comprising the interengageable means having socket means including a vee tooth rack and projection means engageable with said socket means.

7. A force-producing connector for orthodontic headgear including force-reaction means engageable with the head or neck of a wearer, force-applying means for applying force to the wearer's jaw, a helical compression spring, means for applying force produced by the spring to the force-reaction means and the force-applying means, an elongated casing, a generally cylindrical abutment member engageable by the spring and carried by the casing and interengageable means for holding the abutment means relative to the casing in different positions axially of the spring to alter the effective spring length and consequently the force produced by the spring on the force-reaction means and the force-applying means, the improvement comprising the inter- engageable means having arcuate spaced flanges on said generally cylindrical member forming grooves between said flanges forming socket means and projection means engageable with said socket means.

8. The connector defined in claim 7, in which the flanges are circumferentially interrupted by a chordal flat section.

9. The connector defined in claim 7, in which the flanges are of helical thread shape.

10. The connector defined in claim 9, in which the threads are of square thread type.

11. The connector defined in claim 9, in which the threads are of vee thread type.

12. The connector defined in claim 9, and latch means engageable between the helical thread portions and the casing for deterring movement of the helical thread portions relative to the casing.

13. A force-producing connector for orthodontic headgear including force-reaction means engageable with the head or neck of a wearer, force-applying means for applying force to the wearer's jaw, a helical compression spring, means for applying force produced by the spring to the force-reaction means and the force-applying means, a casing, a generally cylindrical abutment member engageable by the spring and carried by the casing and interengageable means for holding the abutment means relative to the casing in different positions axially of the spring to alter the effective spring length and consequently the force produced by the spring on the force-reaction means and the force-applying means, the improvement comprising the generally cylindrical abutment member having external threads, nut means engaged with said threads for moving said generally cylindrical abutment member axially relative to the casing by rotation of said nut means relative to the generally cylindrical abutment member, and means restraining movement of said nut means axially of the generally cylindrical abutment member relative to the casing.

14. The connector defined in claim 13 and means restraining rotation of the generally cylindrical abutment member relative to the casing.

15. A force-producing connector for orthodontic headgear including force-reaction means engageable with the head or neck of a wearer, force-applying means for applying force to the wearer's jaw, a helical compression spring, means for applying force produced by the spring to the force-reaction means and the force-applying means, a casing, abutment means engageable by the spring and carried by the casing and interengageable means for holding the abutment means relative to the casing in different positions axially of the spring to alter the effective spring length and consequently the force produced by the spring on the force-reaction means and the force-applying means, the improvement comprising the interengageable means including a slot in the casing and a pin carried by the abutment means and engaged in said slot.

16. The connector defined in claim 15, in which the casing slot is elongated lengthwise of the spring and the casing has a plurality of notches spaced lengthwise of the casing slot and opening into the casing slot for receiving the pin carried by the abutment means.

* * * * *